(12) United States Patent
Swick (10) Patent No.: US 8,308,678 B2
(45) Date of Patent: Nov. 13, 2012

(54) PRE-FILLED APPLICATOR DEVICE

(75) Inventor: Paul B. Swick, Lebanon, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 164 days.

(21) Appl. No.: 12/236,135

(22) Filed: Sep. 23, 2008

(65) Prior Publication Data

US 2010/0076369 A1    Mar. 25, 2010

(51) Int. Cl.
*A61M 31/00* (2006.01)
*A61M 5/30* (2006.01)
*A61M 25/00* (2006.01)
*A61F 6/00* (2006.01)

(52) U.S. Cl. ............ 604/57; 604/59; 604/60; 604/264; 128/830

(58) Field of Classification Search .............. 604/57–60, 604/187, 272–279, 264, 68–70; 128/830–841
See application file for complete search history.

(56) References Cited

U.S. PATENT DOCUMENTS

| 4,636,202 A | * | 1/1987 | Lowin et al. | 604/236 |
| 4,883,470 A | * | 11/1989 | Haindl | 604/192 |
| 5,282,789 A | | 2/1994 | Lundy | |
| 6,364,854 B1 | | 4/2002 | Ferrer et al. | |
| 2002/0177582 A1 | | 11/2002 | Maloney | |

FOREIGN PATENT DOCUMENTS

| WO | WO 98/34671 | 8/1998 |
| WO | WO 99/21562 | 5/1999 |
| WO | WO 03/070301 A1 | 8/2003 |
| WO | WO 2005/035045 A1 | 4/2005 |
| WO | WO 2006/014572 A1 | 2/2006 |
| WO | WO 2007/044503 A2 | 4/2007 |

* cited by examiner

*Primary Examiner* — Nicholas Lucchesi
*Assistant Examiner* — Rebecca E Eisenberg
(74) *Attorney, Agent, or Firm* — McCarter & English, LLP (57) ABSTRACT

A device for delivering a medicated product or the like to a bodily cavity is provided. The device includes a barrel member having a distal end. The barrel member is sized to contain the medicated product. The device includes a plunger sized to extend into the barrel member. A cap is adapted to move between a sealing position, in which the cap is positioned adjacent to the barrel member and seals the distal end of the barrel member, and a dispensing position, in which the cap is moved in a direction away from the barrel member. The cap includes at least one opening sized to allow the medicated product to flow through the cap when the cap is in the dispensing position. A retainer mechanism is provided for retaining the cap on the barrel when the cap is in the dispensing position.

17 Claims, 13 Drawing Sheets

PRE-FILLED APPLICATOR DEVICE

FIELD OF THE INVENTION

The present invention relates to pre-filled applicator devices and, more particularly, to a pre-filled applicator device for delivering medicated materials to a bodily cavity or passage.

BACKGROUND OF THE INVENTION

Applicators for delivering medicated materials to an internal bodily cavity, such as the vaginal canal, are known. A conventional applicator includes a barrel member for receiving medicated materials, a plunger member for expelling the medicated materials from the barrel member into a bodily cavity, and a cap sized to cover the barrel member.

Some applicators are provided with the medicated materials pre-installed in the barrel member. Some of these applicators require a foil pouch to effectively seal the barrel member. In cases where the medicated materials are not pre-filled, a separate tube containing the medicated materials is provided and the user is directed to load the medicated materials from the separate tube into the applicator. However, it is often difficult to load an accurate dose of the medicated materials from the separate tube into the applicator.

With both types of applicators, the user is typically required to remove the cap from the barrel member to dispense the medicated materials out of a single opening formed at the distal end of the barrel member.

SUMMARY OF THE INVENTION

The present invention relates to a device for delivering a medicated product or the like to a bodily cavity. The device includes a barrel member having a distal end which has an opening and a proximal end. The barrel member is sized to contain the medicated product. The device includes a plunger sized to extend into the barrel member. A cap is adapted to move between a sealing position, in which the cap is positioned adjacent to the barrel member and seals the distal end of the barrel member, and a dispensing position, in which the cap is moved in a direction away from the barrel member. The cap includes at least one opening sized to allow the medicated product to flow through the cap when the cap is in the dispensing position. In this manner, complete removal of the cap is not required to dispense the medicated product from the applicator.

A retainer mechanism is provided for retaining the cap on the barrel when the cap is in the dispensing position. The retainer mechanism prevents the cap from being completely disjointed from the barrel member. A sealing mechanism, such as a piston, is provided for sealing the proximal end of the barrel member.

BRIEF DESCRIPTION OF THE DRAWINGS

For a more complete understanding of the present invention, reference is made to the following Detailed Description of the Invention considered in conjunction with the accompanying drawings, in which.

DETAILED DESCRIPTION OF THE INVENTION

Figure 1:
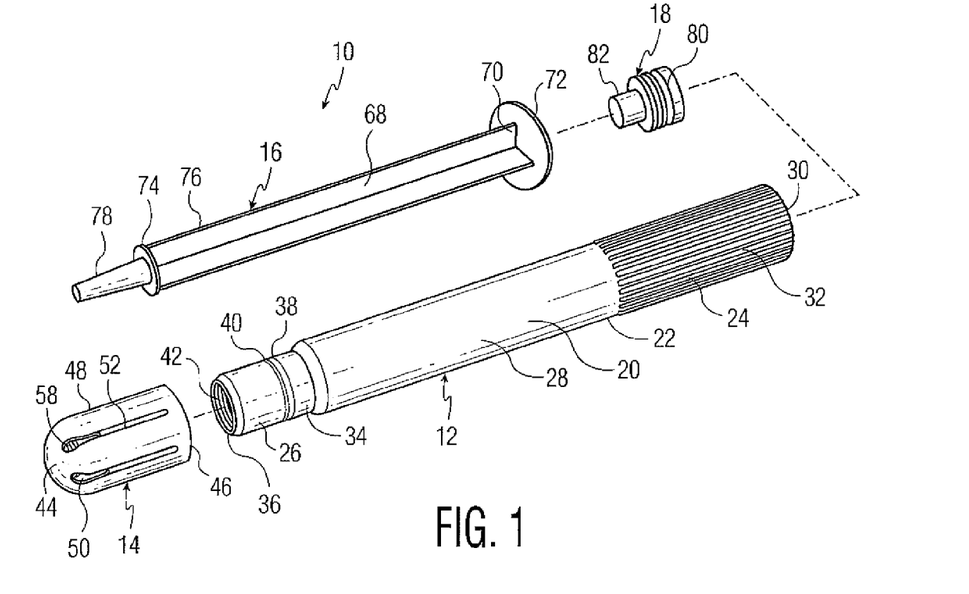
FIG. 1 is an exploded perspective view of an applicator according to the present invention.
Figure 2:
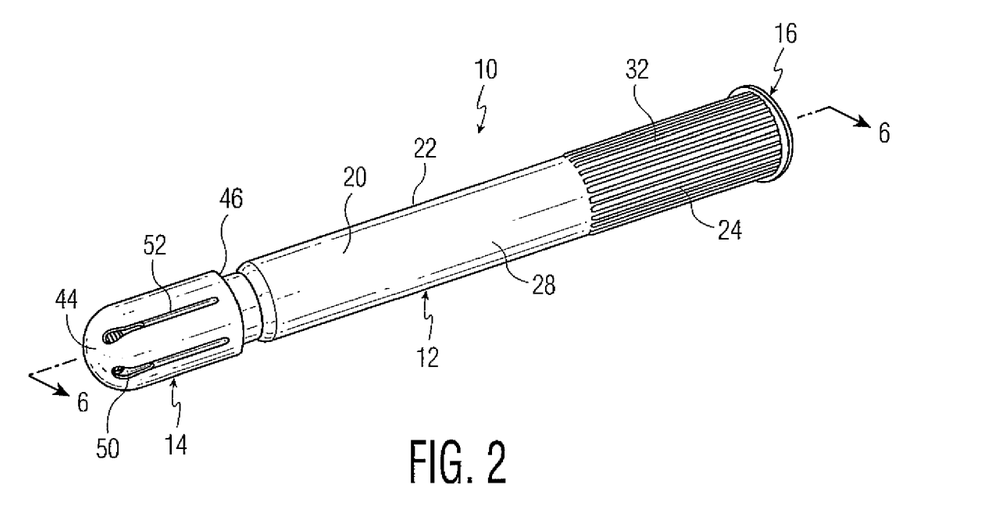
FIG. 2 is a perspective view of the applicator shown in FIG. 1 in an assembled configuration ready for use.

FIG. 1 illustrates an applicator 10 that is adapted for use in delivering pharmaceutical products or medicated materials (e.g., creams, ointments, lubricants, contraceptive gels, etc.) to a bodily cavity, such as a vaginal cavity. The applicator 10 includes a barrel member 12, a screw cap 14, a plunger 16, and a piston 18, each of which can be made from a suitable material (e.g., thermoplastics such as high density polyethylene, low density polyethylene, and linear low density polyethylene, polypropylene, etc.). Other plastic materials can also be used to manufacture the components of the applicator 10.

The barrel member 12 is provided with an interior passageway 20 extending therethrough, and an annular wall 22 defining the passageway 20. The barrel member 12 is sized to contain approximately 5 cc of medicated materials pre-filled in the passageway 20. It will be understood that the applicator 10 can contain other quantities of medicated materials.

The barrel member 12 is provided with a proximal section 24, a distal section 26, and an intermediate section 28 located between the proximal and distal sections 24, 26. The proximal section 24 includes an open end 30, as well as a ribbed surface 32 so as to provide a gripping surface during the use of the applicator 10. The distal section 26 of the barrel member has a proximal end 34, which is adjacent to the intermediate section 28, and an open distal end 36 opposite to the proximal end 34. The distal section 26 has a reduced diameter relative to the proximal and intermediate sections 24, 28 (i.e., the diameter of the distal section 26 is less than that of the proximal and intermediate sections 24, 28). The distal section 26 includes a first annular retention ring 38 and a second annular retention ring 40 for purposes to be discussed hereinafter. More particularly, the first annular retention ring 38 and the second annular retention ring 40 project radially outwardly from the distal section 26.

The distal section 26 of the barrel member 12 includes a series of internal threads 42 (FIGS. 1 and 5-8) proximate to the open distal end 36. The internal threads 42 are sized to threadedly engage and mate with the screw cap 14 for purposes to be discussed hereinafter.

The barrel member 12 is sized to allow for the appropriate amount of medicated materials and to allow for comfortable insertion into the vagina. The barrel member 12 has a length to allow for at least three inches of penetration into the vagina and to allow sufficient space for gripping the proximal section 24 of the barrel member 12 with a user's fingers. More particularly, the barrel member 12 has a length of 4.5 inches and a diameter of approximately 0.5 inches. It will be understood that these dimensions are merely exemplary and that the barrel member 12 can have other dimensions.

Figure 3:
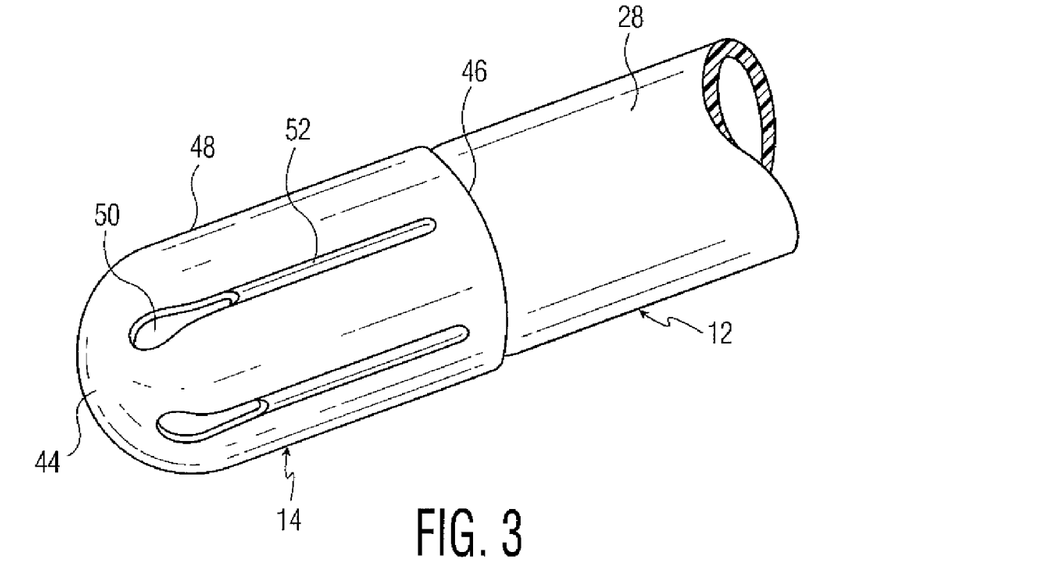
FIG. 3 is a partial perspective view showing the screw cap in a closed, sealing position.
Figure 4:
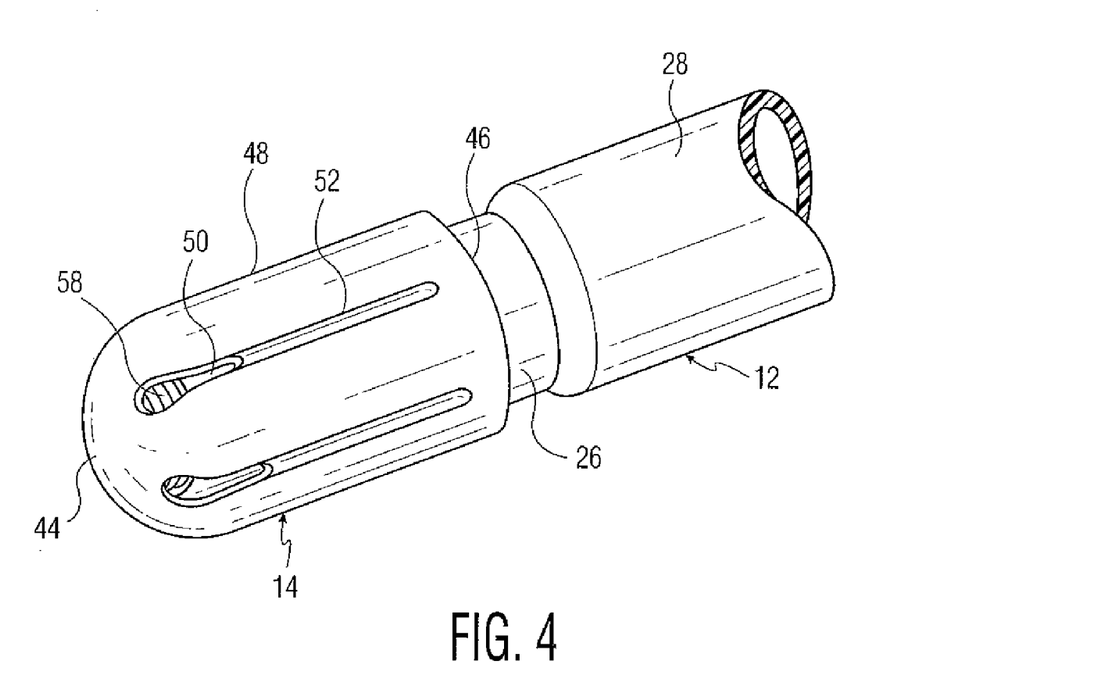
FIG. 4 is a partial perspective view showing the screw cap in an open, dispensing position.

Referring to FIGS. 3 and 4, the screw cap 14 is sized to be moveable relative to the barrel member 12. The screw cap 14 includes a closed insertion end 44 and an opposite open end 46. The screw cap includes an outer wall 48 with a plurality of radially dispersed openings 50 formed along the circumference of the screw cap 14 for allowing the flow of medicated materials therethrough. A plurality of grooves 52 extends from a respective opening 50 along a longitudinal direction toward the open end 46. The grooves 52 are designed for allowing a user to attain a firm grip on the screw cap 14 and to make it easier to rotate the screw cap 14. The grooves 52 also function as flow channels to facilitate in distributing the medicated materials as the medicated materials flow out from the openings 50.

An annular retention bead 54 (see FIGS. 5-9) is formed in the screw cap 14. The annular retention bead 54 projects radially inwardly from an inner surface 56 of the outer wall 48. The annular retention bead 54 cooperates with the first and second retention rings 38, 40 (see FIGS. 1 and 5-9) for purposes to be discussed hereinafter.

The screw cap 14 includes a hollow inner post 58 (see FIGS. 4-8) having a wall 60 positioned within the outer wall 48 of the screw cap 14. As a result of their generally coaxial arrangement, the wall 60 of the hollow inner post 58 and the outer wall 48 of the screw cap 14 cooperate to form an annular space 62 (see FIGS. 6-8) therebetween. The hollow inner post 58 protrudes from the insertion end 44 toward the open end 46 of the screw cap 14, and includes a chamfered end 64 adjacent to the insertion end 44. The hollow inner post 58 includes a plurality of external threads 66 (see FIGS. 4-8) sized to threadedly engage and mate with the internal threads 42 (see FIGS. 1 and 5-8) of the barrel member 12. The external threads 66 and the internal threads 42 cooperate with each other so as to allow the screw cap 14 to be securely connected to the barrel member 12 and to allow relative movement between the screw cap 14 and the barrel member 12, as the screw cap 14 is rotated relative to the barrel member 12.

The screw cap 14 is movable between a closed position (see FIGS. 3 and 5), in which position the screw cap 14 is threaded onto the barrel member 12 and the chamfered end 64 of the hollow inner post 58 serves to seal the open distal end 36 of the barrel member 12, and an open position (see FIGS. 2, 4, and 6-8), in which position the screw cap 14 is unthreaded but retained on the barrel member 12.

Referring to FIG. 1, the plunger 16 is moveably received in the passageway 20 of the barrel member 12 through the proximal section 24 of the barrel member 12. The plunger 16 includes a ribbed shaft 68 having a thumb platform 70 formed at the proximal end 72. The thumb platform 70 has an outer diameter larger than that of the proximal section 24 of the barrel member 12 so as to prevent the thumb platform 72 from being received in the passageway 20, thereby inhibiting the further movement of the plunger 16 toward the distal end 36 of the barrel member 12. The plunger 16 includes a contact platform 74 formed at the distal end 76 with a tapered tip 78 sized to cooperate with the piston 18 for purposes to be described hereinafter. The contact platform 74 has an outer diameter smaller than that of the proximal section 24 of the barrel member 12 so that the contact platform 74 can be inserted into the passageway 20.

Figure 6:
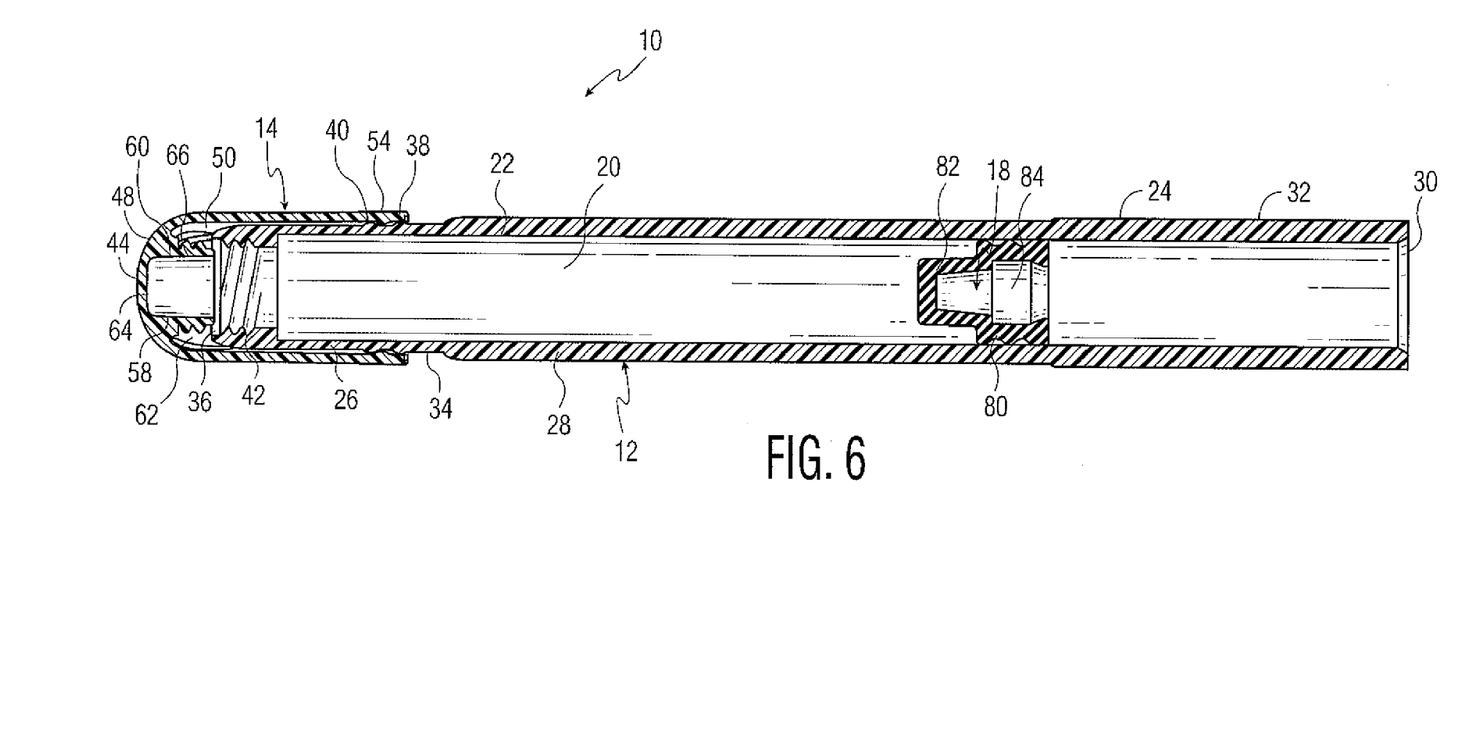
FIG. 6 is a cross-sectional view, taken along section lines 6-6 and looking in the direction of the arrows, of the applicator shown in FIG. 2.

With reference to FIGS. 1 and 6, a closure, such as the piston 18, is pre-installed in the passageway 20 of the barrel member 12 and serves to seal the open proximal end 30 of the barrel member 12 to thereby prevent the medicated materials from flowing therethrough. The piston 18 includes an annular portion 80 and a closed tapered portion 82 extending from the annular portion 80, and an opening 84 (see FIG. 6) formed in the annular portion 80 that is sized to accommodate the tip 78 of the plunger 16. The annular portion 80 is friction-fitted against the wall 22 of the barrel member 12.

Figure 5:
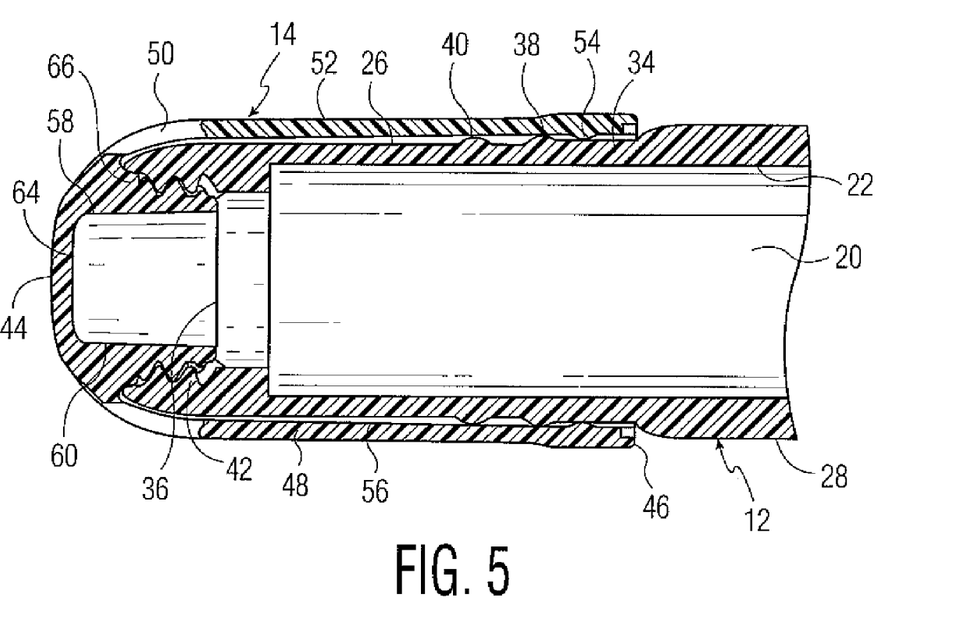
FIG. 5 is a partial cross-sectional view of the screw cap and the barrel member.

With reference to FIG. 5, the applicator 10 is assembled by attaching the screw cap 14 to the barrel member 12 such that the external threads 66 of the hollow inner post 58 of the screw cap 14 mate with the internal threads 42 of the barrel member 12. The applicator 10 is assembled and delivered to the user in this closed position, as shown in FIGS. 3 and 5. The applicator 10 can be provided with the medicated product pre-filled in the passageway 20.

Figure 7:
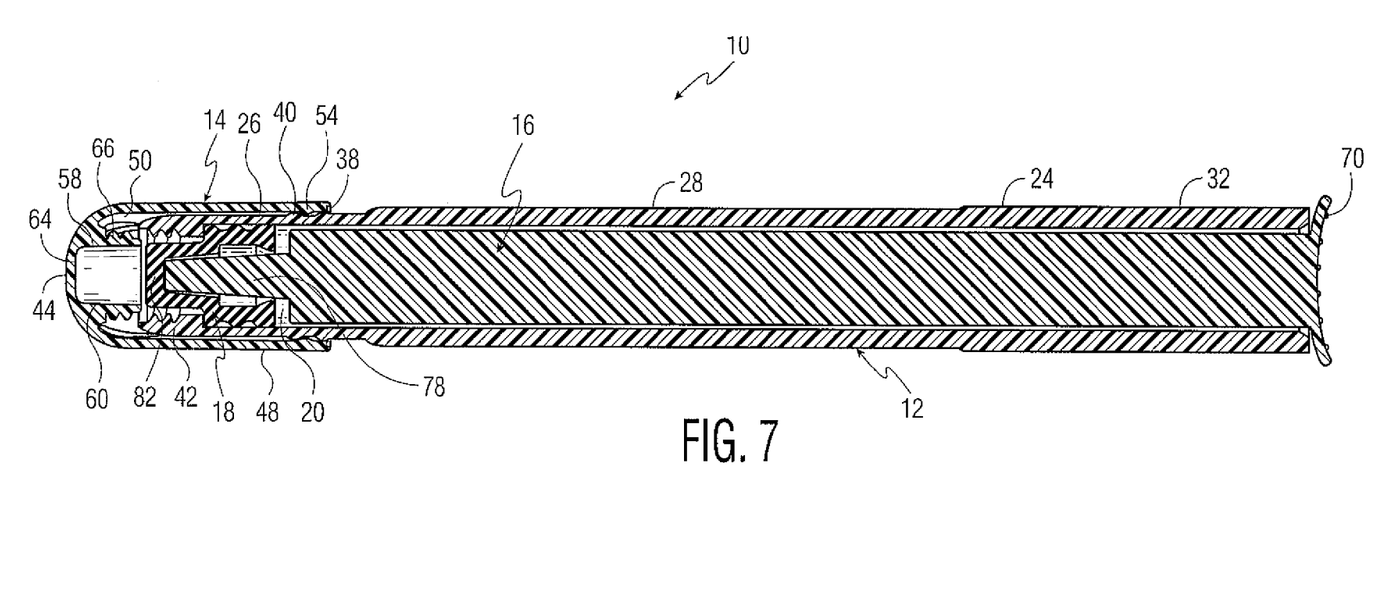
FIG. 7 is a cross-sectional view of the applicator in a dispensing position.
Figure 8:
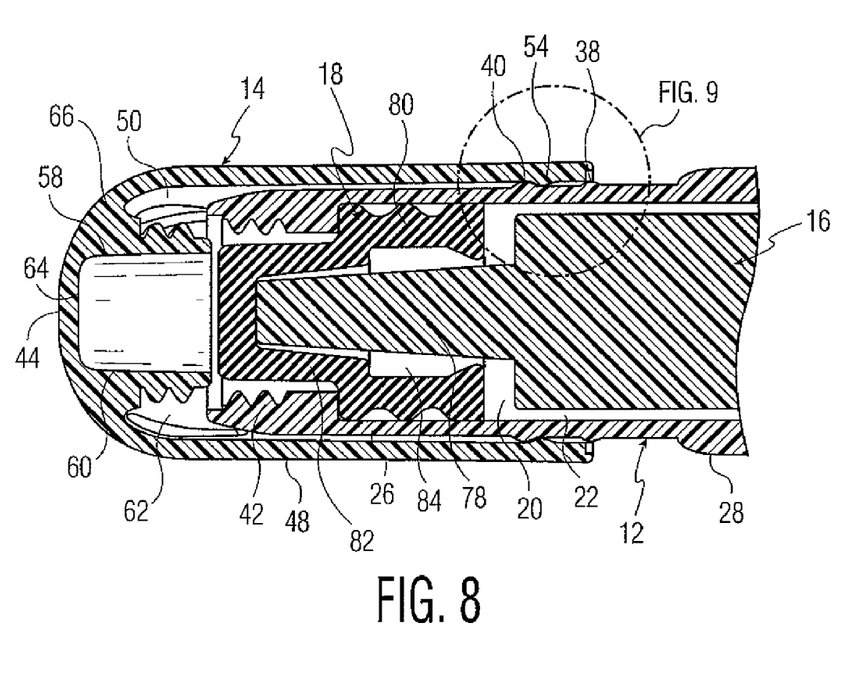
FIG. 8 is a partial cross-sectional view showing the applicator of FIG. 7 in greater detail.
Figure 9:
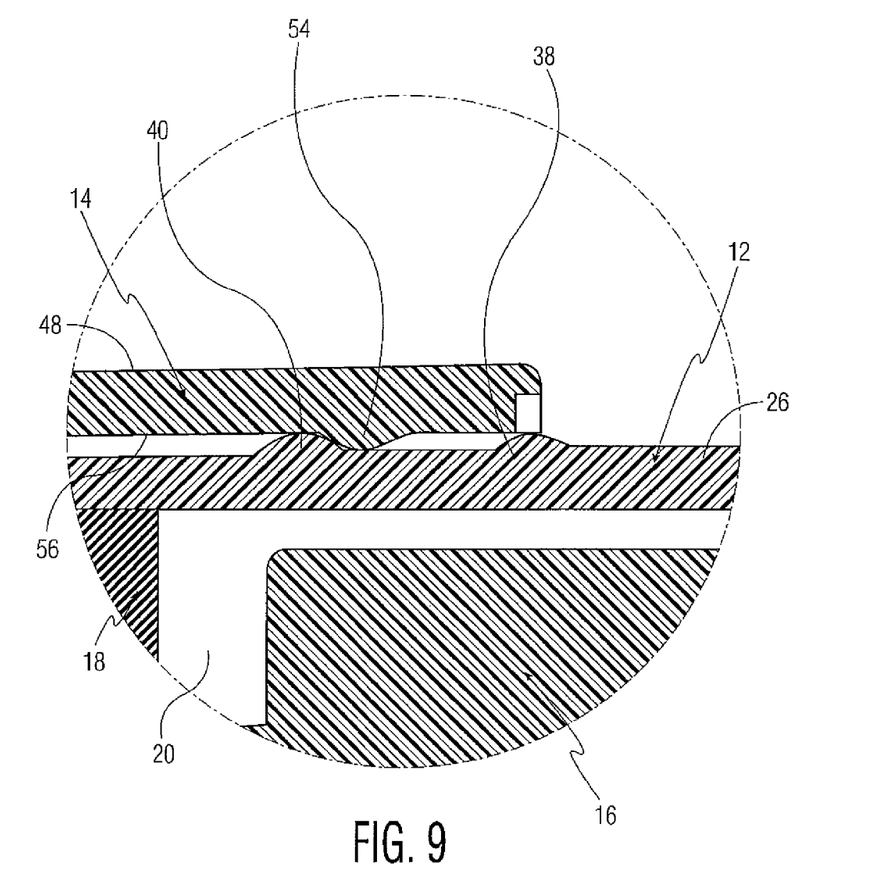
FIG. 9 is a partial cross-sectional view showing the applicator of FIG. 8 in greater detail.

In order to use the pre-filled applicator 10, the screw cap 14 is gripped by the user's fingers and then the screw cap 14 is rotated about 90 to 180 degrees relative to the barrel member 12 in a counterclockwise manner until it overrides the first retention ring 38 formed on the barrel member 12, as shown in FIG. 6. In this open position, the screw cap 14 is captured between the first and second retention rings 38, 40 as best shown in FIG. 9, and the distal end 36 of the barrel member 12 and the openings 50 in the screw cap 14 are exposed as shown in FIGS. 6-8. The retention bead 54 formed on the screw cap 14 and the second retention ring 40 formed on the barrel member 12 cooperate to prevent the screw cap 14 from overriding the second retention ring 40, thereby retaining the screw cap 14 on the barrel member 12. The retention bead 54 and the first retention ring 38 cooperate to prevent the screw cap 12 from overriding the first retention ring 38 to move back toward the barrel member 12, thereby preventing the barrel member 12 from resealing prior to delivery of the medicated materials. Thus, the retention bead 54 and the first and second retention rings 38, 40 serve as stops by limiting the axial movement of the screw cap 12. Needless to say, the present invention could also be configured such that the screw cap 14 moves in a clockwise manner. Thus, the present invention is not limited by the term "counterclockwise."

The screw cap 14 and the distal section 26 of the barrel member 12 are then inserted into a vaginal canal (not shown) in a conventional manner. In doing so, the barrel member 12 is gripped by the user's fingers at the ribbed surface 32 of the proximal section 24. After properly placing the distal section 26 of the barrel member 12 in the vaginal canal, the thumb platform 70 of the plunger 16 is pushed toward the piston 18 so as to move the piston 18 and the plunger 16 toward the distal end 36 of the barrel member 12, as shown in FIGS. 7 and 8. In this regard, the applicator 10 can be held and operated by the user in any conventional manner. For instance, with the proximal section 24 of the barrel member 12 held by the user's index and middle fingers, the thumb platform 70 of the plunger 16 can be pushed by the user's thumb. As the piston 18 and the plunger 16 move toward the distal end 36 of the barrel member 12, the piston 18 pushes the medicated product toward the screw cap 14 where the medicated product is radially released through the openings 50 formed in the screw cap 14. The grooves 52 facilitate to distribute the medicated product forward and backward along the vaginal canal. In order to ensure the full release of the medicated product from the applicator 10, the plunger 16 is pushed until the thumb platform 70 is positioned adjacent to the proximal open end 30 of the barrel member 12. After the release of the medicated product from the applicator 10 into the vaginal canal, the applicator 10 is removed from the vaginal cavity. The applicator 10 is then discarded or cleaned and disinfected for subsequent use.

It should be appreciated that the applicator 10 of the present invention provides numerous advantages over conventional applicators. For instance, the screw cap 14 serves to seal the distal end 36 of the barrel member 12, which maintains the long term stability of the medicated materials by providing a moisture and gas barrier. The screw cap 14 also functions as a nozzle to distribute the medicated materials in a radial manner. The applicator 10 is adaptable to current pre-filled applicator technology. Because the applicator 10 is pre-filled with medicated materials, it is not necessary to fill the applicator 10 with medicated materials from a separate tube.

It should be noted that the applicator 10 of the present invention can have numerous modifications and variations. For instance, the applicator 10 can be provided with a barrel member 12 having external threads (not shown) and an inner post 58 having inner threads (not shown) that are sized to threadedly engage and mate with the external threads. The applicator 10 can be provided with any suitable mechanism for preventing the screw cap 14 from inadvertently falling off from the barrel member 12 while in use. The applicator 10 can be modified to include a single opening (not shown) in the screw cap 14. Although the present invention is especially suitable for use in delivering medicated materials to vaginal canals or cavities, it can be used to dispense medicated materials or other pharmacological products in other body cavities such as a rectum. The screw cap 14 can be rounded, bullet shaped, or conical at the insertion end 44 to facilitate insertion of the applicator 10. The distal section 26 of the barrel member 12 could include a distal subsection, a proximal subsection, a slightly tapered intermediate subsection positioned between the distal and proximal subsections, and a single retention ring positioned at the intersection of the distal and intermediate subsections. The plunger 16 could serve as a closure to seal off the proximal end 30 of the barrel member 12.

Figure 10:
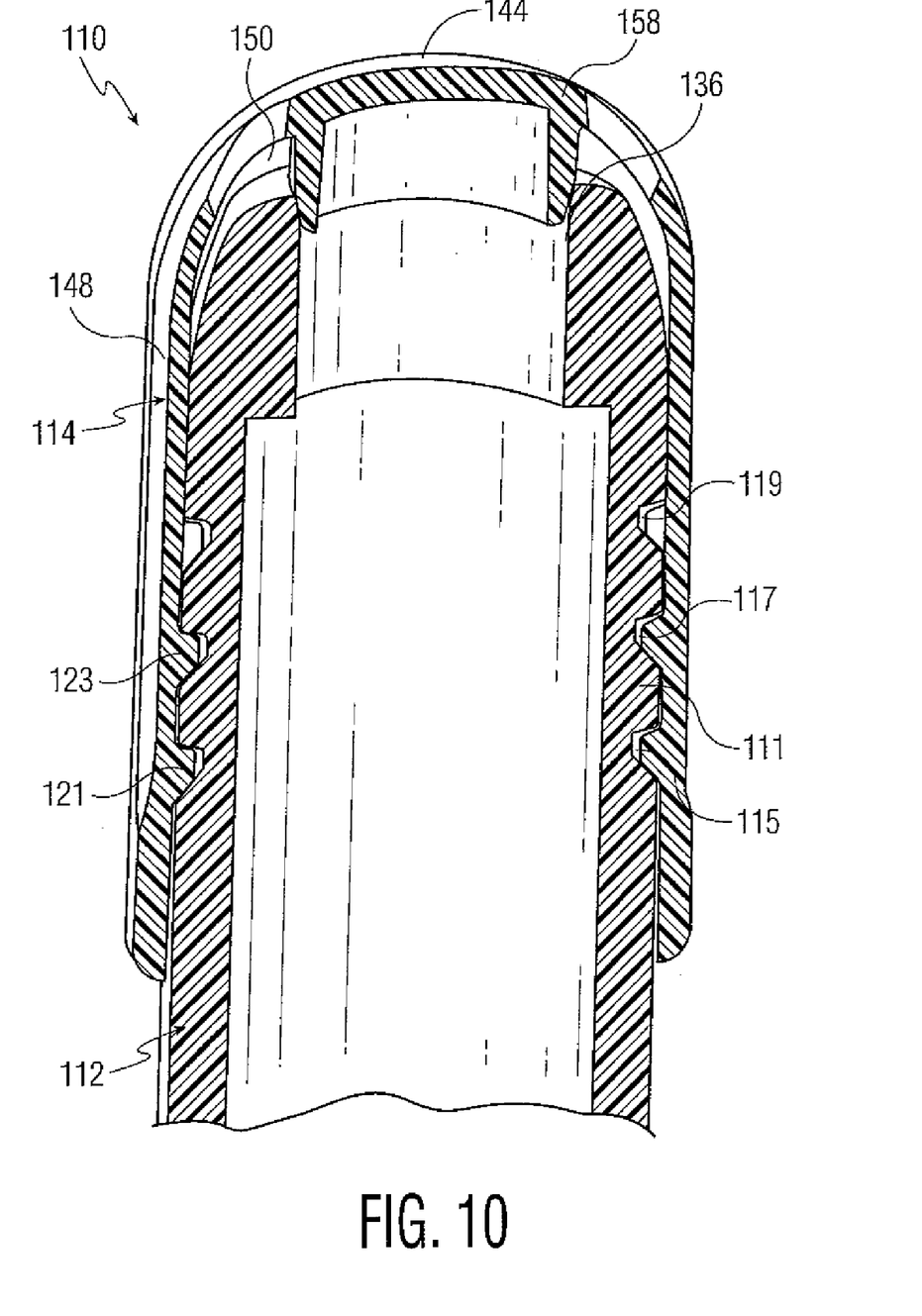
FIG. 10 is a partial cross-sectional view showing another embodiment of the applicator of the present invention, which includes a barrel member having external threads and a screw cap with internal threads.

FIG. 10 shows another embodiment of an applicator, indicated generally as 110, that operates and is constructed in manners consistent with the applicator 10 shown in FIGS. 1-9, unless stated otherwise. The applicator 110 includes a barrel member 112 having external threads 111 with an initial channel 115, an intermediate channel 117, and a terminal channel 119.

The screw cap 114 includes an insertion end 144 and a plurality of openings 150 formed along the circumference of the screw cap 114. A hollow inner post 158 protrudes from the insertion end 144 and serves to seal the open distal end 136 of the barrel member 112. The screw cap 114 includes an outer wall 148 with a first internal thread 121 and a second internal thread 123, which are sized to threadedly engage and mate with the external threads 111 of the barrel member 112. The external threads 111 and the first and second internal threads 121, 123 cooperate with each other so as to allow the screw cap 114 to be securely connected to the barrel member 112 and to allow relative movement between the screw cap 114 and the barrel member 112, as the screw cap 114 is rotated relative to the barrel member 112.

The screw cap 114 is movable between a closed position (see FIG. 10), in which position the first internal thread 121 is engaged with the initial channel 115 and the second internal thread 123 is engaged with the intermediate channel 117, and an open position (not shown), in which position the first internal thread 121 is engaged with the intermediate channel 117 and the second internal thread 123 is engaged with the terminal channel 119.

The applicator 110 is assembled by attaching the screw cap 114 to the barrel member 112 such that the first and second threads 121, 123 formed on the screw cap 114 mate with the external threads 111 formed on the barrel member 112. The applicator 110 is assembled and delivered to the user in this closed position, as shown in FIG. 10.

In order to use the pre-filled applicator 110, the screw cap 114 is gripped by the user's fingers and then the screw cap 114 is rotated relative to the barrel member 112 in a counterclockwise manner until the screw cap 114 assumes its open position. Because the external threads 111 do not extend beyond the terminal channel 119, the screw cap 114 remains threaded on the barrel member 112 as the screw cap 112 is rotated. As a result, further rotation of the screw cap 114 in a counterclockwise manner is impeded, thereby retaining the screw cap 114 on the barrel member 112.

Figure 11:
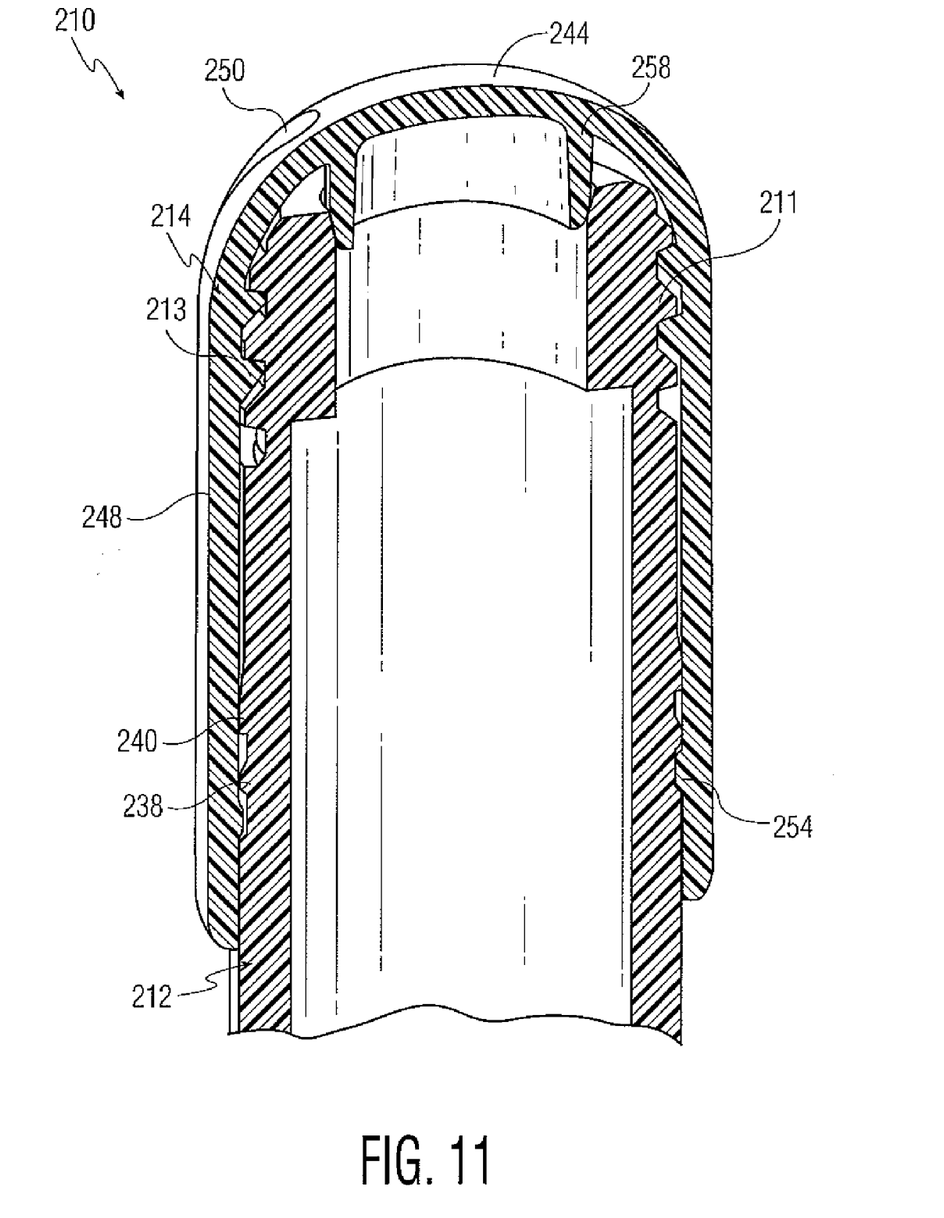
FIG. 11 is a partial cross-sectional view of an applicator showing another embodiment of the applicator of the present invention, which includes a barrel member having external threads and retention rings, and a screw cap with internal threads and a retention bead.

FIG. 11 shows another embodiment of an applicator, indicated generally as 210, that operates and is constructed in manners consistent with the applicator 10 shown in FIGS. 1-9, unless stated otherwise. The applicator 210 includes a barrel member 212 having external threads 211, a first retention ring 238, and a second retention ring 240.

Like the screw cap 114 of the applicator 110, the screw cap 214 includes an insertion end 244, a plurality of openings 250, and an inner post 258. The screw cap 214 includes an outer wall 248 with a plurality of internal threads 213 which are sized to threadedly engage and mate with the external threads 211 of the barrel member 214. A retention bead 254 is formed in the screw cap 214.

The applicator 210 is assembled by attaching the screw cap 214 to the barrel member 212 such that the internal threads 213 formed on the screw cap 214 mate with the external threads 211 formed on the barrel member 212. The applicator 210 is assembled and delivered to the user in this closed position, as shown in FIG. 11.

In order to use the pre-filled applicator 210, the screw cap 214 is gripped by the user's fingers and then the screw cap 214 is rotated relative to the barrel member 212 in a counterclockwise manner until it overrides the first retention ring 238 formed on the barrel member 214. In this open position (not shown), the screw cap 214 is captured between the first and second retention rings 238, 240. The retention bead 254 formed on the screw cap 214 and the second retention ring 240 formed on the barrel member 212 cooperate to prevent the screw cap 214 from overriding the second retention ring 240, thereby retaining the screw cap 214 on the barrel member 212. The retention bead 254 and the first retention ring 238 cooperate to prevent the screw cap 214 from overriding the first retention ring 238 to move back toward the barrel member 212, thereby preventing the barrel member 212 from resealing prior to delivery of the medicated materials.

Figure 12:
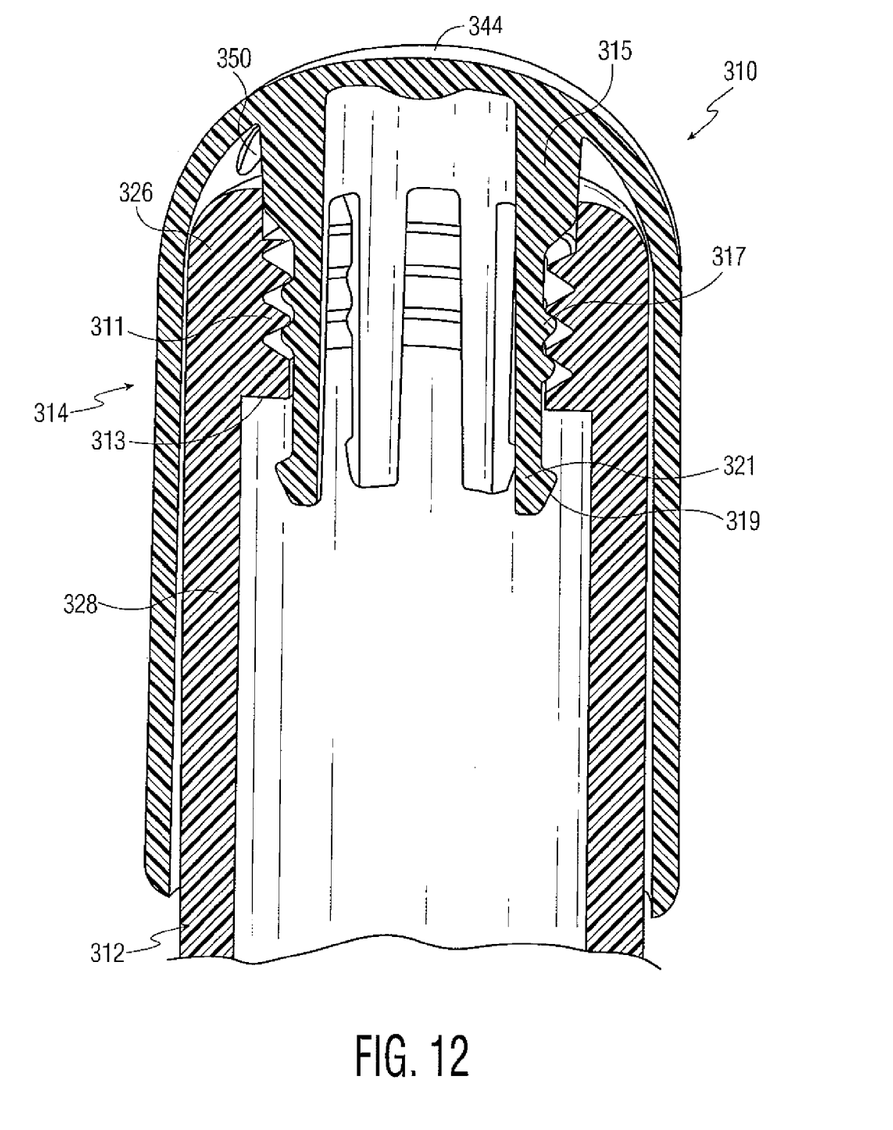
FIGS. 12 and 13 are partial cross-sectional views of an applicator showing another embodiment of the applicator of the present invention, which includes a screw cap with prongs having external threads.
Figure 13:
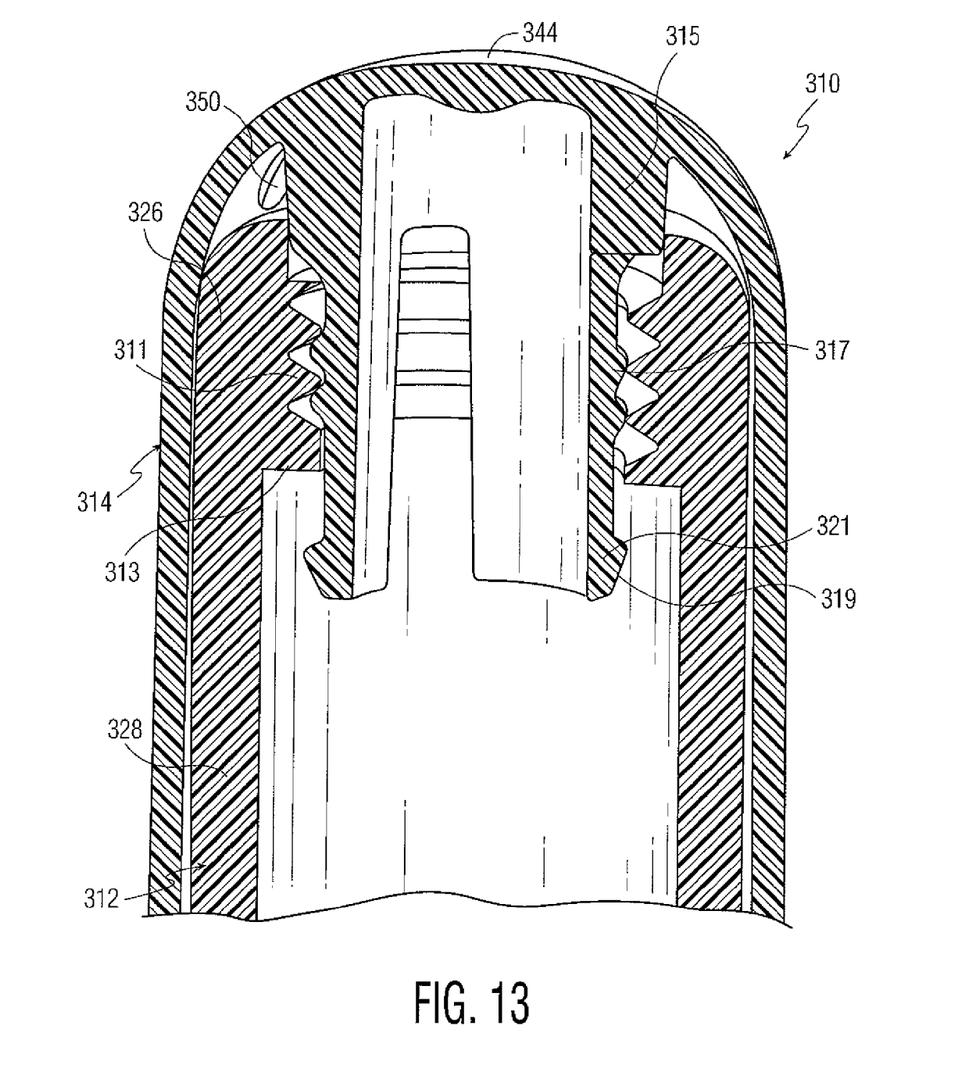

FIGS. 12 and 13 show another embodiment of an applicator, indicated generally as 310, that operates and is constructed in manners consistent with the applicator 10 shown in FIGS. 1-9, unless stated otherwise. The applicator 310 includes a barrel member 312 having a plurality of internal threads 311 and a shoulder 313 formed at the intersection of the distal section 326 and the intermediate section 328. The shoulder 313 serves as a stop, as will be described in further detail below.

The screw cap 314 includes an insertion end 344 and a plurality of openings 350. A plurality of prongs 315 extends from the insertion end 344. The prongs 315 include external threads 317 which are sized to threadedly engage and mate with the internal threads 311 of the barrel member 312. Retention lugs 319 are formed on the free end 321 of each of the prongs 315. The retention lugs 319 project radially outwardly from the free ends 321 of the prongs 315. The number of prongs 315 can vary. For example, the applicator 310 shown in FIG. 13 employs fewer prongs 315 than that of the applicator 310 shown in FIG. 12.

The applicator 310 is assembled by attaching the screw cap 314 to the barrel member 312 such that the internal threads 311 formed on the barrel member 312 mate with the external threads 317 formed on the screw cap 314. The applicator 310 is assembled and delivered to the user in this closed position, as shown in FIGS. 12 and 13.

In order to use the pre-filled applicator 310, the screw cap 314 is gripped by the user's fingers and then the screw cap 314 is rotated relative to the barrel member 312 in a counterclockwise manner until the retention lugs 319 contact the shoulder 313 of the barrel member 312. The retention lugs 319 cooperate with the shoulder 313 to impede further rotation of the screw cap 314 in a counterclockwise manner, which retains the screw cap 314 on the barrel member 312.

Figure 14:
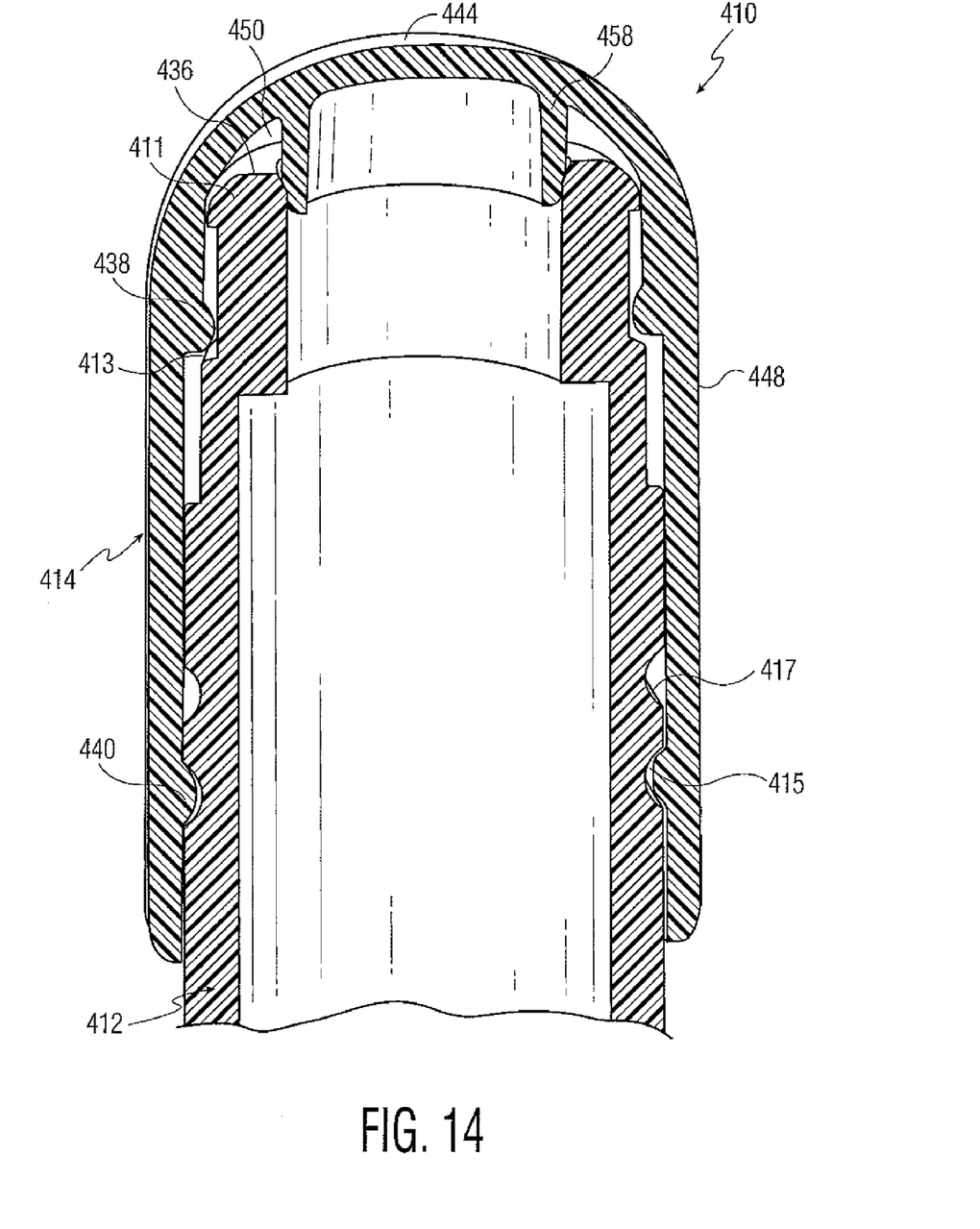
FIG. 14 is a partial cross-sectional view of an applicator showing another embodiment of the applicator of the present invention, which includes a screw cap that is sized to be snap-fitted onto the barrel member.

FIG. 14 shows another embodiment of an applicator, indicated generally as 410, that operates and is constructed in manners consistent with the applicator 10 shown in FIGS. 1-9, unless stated otherwise. The applicator 410 includes a barrel member 412 with a flange portion 411 at the distal end 436 and a shoulder 413 formed proximate to the distal end 436. The barrel member 414 includes first and second grooves 415, 417.

The screw cap 414 includes an insertion end 444, a plurality of openings 450, and an inner post 458. The screw cap 414 includes an outer wall 448 with a first retention bead 438 and a second retention bead 440.

The applicator 410 is assembled by attaching the screw cap 414 to the barrel member 412 such that the first retention bead 438 is positioned between the flange portion 411 and the shoulder 413 while the second retention bead 440 is snap fitted in the first groove 415. The applicator 410 is assembled and delivered to the user in this closed position, as shown in FIG. 14.

In order to use the pre-filled applicator 410, the outer wall 448 of the screw cap 414 is pulled radially outwardly to remove the second retention bead 440 from the first groove 415. The screw cap 414 is pushed in an axial direction until the first retention bead 438 contacts the flange portion 411 of the barrel member 412. The second retention bead 440 is then snap-fitted in the second groove 417, which retains the screw cap 414 on the barrel member 412.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined by the appended claims.

What is claimed is:

1. A device for delivering a medicated product to a bodily cavity, comprising:

a barrel member having a distal end and a proximal end, said barrel member sized to contain the medicated product;

a plunger sized to extend into said proximal end of said barrel member;

a cap adapted to move between a sealing position, in which said cap is positioned adjacent to said barrel member and seals said distal end of said barrel member, and a dispensing position, in which said cap is moved in a direction away from said barrel member, said cap including an opening sized to allow the medicated product to flow through said cap when said cap is in said dispensing position, said barrel member including a plurality of internal threads, said cap including a plurality of external threads sized to threadedly mate with said internal threads of said barrel member, said internal threads of said barrel member and said external threads of said cap cooperating with each other so as to allow said cap to move from said sealing position to said dispensing position upon rotational movement of the cap; and retainer means for retaining said cap on said barrel member when said cap is in said dispensing position.

2. The device of claim 1, further comprising sealing means for sealing said proximal end of said barrel member.

3. The device of claim 2, wherein said retaining means includes a first retention ring and a second retention ring, each of said first and second retention rings projecting from said barrel member, and a retention bead projecting from said cap, said retention bead sized to engage said first and second retention rings.

4. The device of claim 3, wherein said cap is captured between said first and second retention rings when said cap is in said dispensing position.

5. The device of claim 4, wherein said cap is sized to override said first retention ring as said cap moves to said dispensing position, said retention bead and said second retention ring cooperating to prevent said cap from overriding said second retention ring, and said retention bead and said first retention ring cooperating to prevent said cap from overriding said first retention ring after said cap is in said dispensing position.

6. The device of claim 5, wherein said cap includes an outer wall and a post protruding toward said barrel member, said post including said external threads.

7. The device of claim 6, wherein said cap includes a plurality of radial openings formed along the circumference of said cap, said openings sized to allow the medicated product to flow through said cap when said cap is in said dispensing position.

8. The device of claim 7, wherein said cap includes a plurality of longitudinally extending grooves, each of said grooves sized to extend from one of said openings.

9. The device of claim 8, wherein said sealing means includes a piston positioned in said barrel member.

10. The device of claim 9, wherein said plunger includes a distal end and a contact platform formed at said distal end of said plunger, and a proximal end and a thumb platform formed at said proximal end of said plunger.

11. The device of claim 10, wherein said plunger is axially moveable relative to said barrel member so as to move said piston from a first position, in which position said piston is positioned adjacent to said proximal end of said barrel member, to a second position, in which said piston is positioned adjacent to said distal end of said barrel member so as to expel the medicated product from said barrel member to said openings in said cap.

12. The device of claim 11, wherein said thumb platform is sized to engage said proximal end of said barrel member so as to restrict said plunger from moving said piston beyond said second position.

13. A device for delivering a medicated product to a bodily cavity, comprising:
 a barrel member having a distal end and a proximal end, said barrel member sized to contain the medicated product;
 a plunger sized to extend into said proximal end of said barrel member;
 a closure for sealing said proximal end of said barrel member;
 a cap adapted to move between a sealing position, in which said cap is positioned adjacent to said barrel member, and a dispensing position, in which said cap is moved in a direction away from said barrel member, said cap including an opening sized to allow the medicated product to flow through said cap when said cap is in said dispensing position, said barrel member including a plurality of internal threads, said cap including a plurality of external threads sized to threadedly mate with said internal threads of said barrel member, said internal threads of said barrel member and said external threads of said cap cooperating with each other so as to allow said cap to move from said sealing position to said dispensing position upon rotational movement of the cap; and
 a retainer sized to prevent said cap from being removed from said barrel member.

14. An assembly comprising:
 a medicated product; and
 a device for delivering said medicated product to a bodily cavity, said device including
 a barrel member having a distal end, a proximal end, and a passageway sized to contain said medicated product,
 a piston positioned in said barrel member and sized to seal said proximal end of said barrel member,
 a plunger sized to extend into said proximal end of said barrel member, and
 a cap adapted to move between a sealing position, in which said cap is positioned adjacent to said barrel member, and a dispensing position, in which said cap is moved in a direction away from said barrel member, said cap including an opening sized to allow said medicated product to flow through said cap when said cap is in said dispensing position, said barrel member including a plurality of internal threads, said cap including a plurality of external threads sized to threadedly mate with said internal threads of said barrel member, said internal threads of said barrel member and said external threads of said cap cooperating with each other so as to allow said cap to move from said sealing position to said dispensing position upon rotational movement of the cap.

15. The assembly of claim 14, further comprising retainer means for retaining said cap on said barrel member when said cap is in said dispensing position.

16. The assembly of claim 14, wherein the cap moves from said sealing position to said dispensing position when the cap is rotated relative to the barrel member.

17. The assembly of claim 14, wherein the cap moves from said sealing position to said dispensing position when the cap is rotated about 90 degrees to 180 degrees relative to the barrel member.

* * * * *